US005721109A

United States Patent [19]
Yano et al.

[11] Patent Number: 5,721,109
[45] Date of Patent: Feb. 24, 1998

[54] METHOD FOR DIAGNOSING INFECTION CAUSED BY ACID-FAST BACTERIUM

[75] Inventors: Ikuya Yano, Minoh; Shiro Oka, Takaishi; Yoshiteru Ueno, Toyonaka; Yayoi Natsuhara, Osaka; Junji Yoshinaga, Neyagawa; Yoshiko Kato, Nishinomiya, all of Japan

[73] Assignees: Sawai Pharmaceutical Co., Ltd., Osaka; Medisa Shinyaku Inc., Tokyo, both of Japan

[21] Appl. No.: 110,764

[22] Filed: Aug. 23, 1993

Related U.S. Application Data

[63] Continuation of Ser. No. 566,476, Aug. 17, 1990.

[30]      Foreign Application Priority Data

Jan. 18, 1989 [JP] Japan ..................................... 1-10356
Apr. 1, 1989 [JP] Japan ..................................... 1-83836

[51] Int. Cl.$^6$ .................. G01N 33/569; G01N 33/53; C07C 69/00
[52] U.S. Cl. .................. 435/7.32; 435/7.95; 435/7.92; 436/518; 436/531; 436/805; 436/811; 536/4.1; 536/115; 536/119; 554/1; 560/129
[58] Field of Search ................ 435/7.32, 7.95, 435/7.92; 436/518, 531, 805, 811; 536/4.1, 115, 119; 554/1; 560/129

[56]          References Cited

U.S. PATENT DOCUMENTS

| | | | |
|---|---|---|---|
| 4,243,663 | 1/1981 | Azuma et al. | 424/181 |
| 4,307,229 | 12/1981 | Liav et al. | 536/119 |
| 4,401,658 | 8/1983 | Bouchaudon et al. | 424/177 |
| 4,666,851 | 5/1987 | Lee | 435/7.32 |
| 4,806,350 | 2/1989 | Gerber | 424/92 |
| 5,006,464 | 4/1991 | Chu et al. | 436/808 |
| 5,049,664 | 9/1991 | Yoshinaga et al. | 536/119 |
| 5,344,759 | 9/1994 | Laszlo et al. | 435/7.32 |

OTHER PUBLICATIONS

Kaneda et al, "Granuloma Formation & Hemopiesis Induced by Carbon 36–48–Mycolic Acid–containing Glycolipids from Nocardia Rubra", Infect. Immun., 54 (3), 1986, pp. 869–875.

Kato, 1972. Antibody Formation to Trehalose–6–6'–dimycolate (Cord Factor) of Mycobacterium tuberculosis. Infect. Immun. 5: 203–212.

Reggiardo et al, 1980. Elisa Tests for Antibodies Against Mycobacterial Glycolipids, J Immunol. Meth 34: 55–60.

Reggiardo et al, 1981. Comparison of Enzyme–Linked Immunosorbent Assay and Hemagglutination Test Using Mycobacterial Glycolipids, J Clin Microbiol 13: 1007–9.

Smolarsky, 1980, A Simple Radioimmunoassay to Determine Binding of Antibodies to Lipid Antigens, J. Immunol. Meth 38: 85–93.

Mehta et al, 1987. Immune Responses to Sulpholipids of Mycobacterium tuberculosis $H_{37}R_v$. Indian J Med Res 86: 558–63.

Bellanti, 1971. Immunology, W. B Saunders Co., Philadelphia, pp. 99–100.

Daniel et al, 1987. The Serodiagnoses of Tuberculosis and Other Mycobacterial Diseases by Enzyme–Linked Immunosorbent Assay. Am Rev Respir Dis 135: 1137–1151.

Kato, "Antibody Formation to Trehalose–6–6'–Dimycolate (Cord Factor) of Mycobacterium tuberculosis", Infection and Immunity vol. 5, pp. 203–212 (1972).

Kato, "Immunochemical Properties of Anti–Cord Factor Antibody", Infection and Immunity, vol. 7, pp. 9 to 13, 1973.

Yano, "A study on the antibody production of glycolipid containing mycolic acid", Japanese Journal of Bacteriology, vol. 44, No. 1, p. 400 (1989).

Japanese Journal of Bacteriology, vol. 44, No. 2, 1989, pp. 533–539.

Cruaud et al., "Human IgG antibodies immunoreacting with specific sulfolipids from Mycobacterium tuberculosis", Int. J. Med. Microbiol. (Zbl. Bakt.), vol. 271/4, pp. 481–485 (1989).

Goren, "Handbook of Lipid Research," vol. 6, pp. 412, 413, 415, 416, 1990.

Reggiardo, Infection and Immunity, pp. 1369 to 1374, Dec. 1976.

Kato, Infection and Immunity, pp. 9 to 13, Jan. 1973.

Kato, Characterization of Anti–Cord factor Antibody, Symposium, pp. 23 to 26, 1973.

Runyon et al, 1980. "Mycobacterium" in Manual of Clinical Microbiology, (E.H. Lennette et al, eds.) American Society for Microbiology, Washington. pp. 150–151.

Goren, 1990. "Mycobacterial Fatty Acids Esters of Sugars and Sulfosugars", in Handbook of Lipid Research. vol. 6. (M. Kates, ed.) Plenum Press, New York. pp. 363–445.

Chan et al, 1990. Am Rev Respir Dis 142: 385–389.

Minnikin et al, 1985. J Gen Microbiol 131: 1369–1374.

Besra et al, 1992. Biochemistry 31: 9832–9837.

Primary Examiner—James C. Housel
Assistant Examiner—Rodney P. Swartz
Attorney, Agent, or Firm—Jacobson, Price, Holman & Stern, PLLC

[57]          ABSTRACT

A reagent for the detection of an antibody against an acid-fast bacterial antigen comprising at least one compound selected from the group comprising mycolic acids, mycolic acid salts, mycolic acid esters and esters of fatty acids having a carbon number of 14 or more other than mycolic acid with a mono- or disaccharide, a method of detecting an antibody against an acid-fast bacterial antigen using said reagent and a method of diagnosis of acid-fast bacterial infections by said detection method are simpler in procedures and offer much higher specificity in comparison with conventional reagents and methods, enabling identification of acid-fast bacterial genera (including the genera Mycobacterium, Nocardia and Rhodococcus) and acid-fast bacterial species, and thus it is possible to make diagnoses to identify the infecting acid-fast bacterium, which leads to the quick choice of therapeutic drug for the disease.

18 Claims, 7 Drawing Sheets

METHOD FOR DIAGNOSING INFECTION CAUSED BY ACID-FAST BACTERIUM

This application is a continuation of application Ser. No. 07/566,476, filed Aug. 17, 1990.

TECHNICAL FIELD

The present invention relates to a reagent for the specific detection of an antibody against an acid-fast bacterial antigen contained in serum, etc., of humans and other animals infected with tubercule bacillus or an acid-fast bacterium related thereto, a method of detecting an antibody against an acid-fast bacterial antigen, and a method of a quick diagnosis of acid-fast bacterial infections.

BACKGROUND ART

The acid-fast bacteria are characterized by the presence of mycolic acid, an extremely highly hydrophobic long-chain fatty acid, on the surface layer of cells thereof. The mycolic acid exists as bound to various lipids, saccharides, peptides and other substances as well as arabinogalactan.

Above all, trehalose dimycolate (hereinafter abbreviated as TDM), a mycolic acid bound to saccharide, also known as the cord factor in tubercule bacillus, once drew much attention as a toxic glycolipid produced by human tubercule bacillus from the viewpoint of its close relationship with the pathogenicity of the bacillus. In recent years, it has been found that TDM is also widely distributed in the cell walls of a large number of other bacterial species of the genus Mycobacterium and nonpathogenic actinomycetes closely related thereto, such as those belonging to the genera Nocardia and Rhodococcus.

It is also known that the mycolic acid found in the cell walls of acid-fast bacteria occurs not only as TDM but also as mycolic acid containing glycolipids (hereinafter abbreviated as MGL), such as glucose-monomycolate, glucose-dimycolate, fructose-monomycolate, arabinose-monomycolate, mannose-monomycolate, trehalose-monomycolate, trehalose-trimycolate and trehalose-tetramycolate.

These MGLs have drawn much attention in that they possess a wide variety of immunopharmacological bioactivities, such as immunoadjuvant activities, non-specific protective immunity, granuloma formation capability, macrophage-activating capability and antitumor activities, as well as toxicity [cf. Kekkaku, 63 (3), 41–54 (1988) and the Proceedings of the 11th Meeting of the Japanese Society for Medical Mass Spectrometry, 11, 63–72 (1986)].

A particular kind of mycolic acid is specific to bacterial species, which serve as an important factor for identification of acid-fast bacteria. Meanwhile, there have already been elucidated the subclass composition and molecular species composition of mycolic acid for each bacterial species [cf. the Journal of Clinical Microbiology, 24 (6), 106–1070 (1986) and the Journal of General Microbiology, 134, 2213–2229 (1988)].

It is therefore possible to identify acid-fast bacteria, namely, infecting bacterial species, by detecting the antibody against the mycolic acid derived from each bacterial species or its derivative.

However, since these bacterial species have conventionally been identified mainly by analyzing the morphological and biochemical characters of bacterial cells obtained after isolation culture, this identification method has posed problems, such as lack of speed and unsatisfactory reliability of results due to inconsistent evaluation of results obtained in some species.

It is a well-known fact that infections with tubercule bacillus or acid-fast bacteria closely related thereto proceed mainly with epithelioid cellular granuloma based various immunological reactions and cause tubercules and cavitation, the most characteristic lesions. However, there is no method for quick identification of these infectious bacteria. With this background, there is a strong demand for a method of the quick diagnosis of these infections with tubercule bacillus or acid-fast bacteria closely related thereto.

It is an object of the present invention to provide a reagent for identification of acid-fast bacterial species and acid-fast bacterial genera (including the genera Mycobacterium, Nocardia and Rhodococcus).

It is another object of the present invention to provide a method of identification of acid-fast bacterial species and acid-fast bacterial genera (including the genera Mycobacterium, Nocardia and Rhodococcus.).

It is yet another object of the present invention to provide a method of quick diagnosis of acid-fast bacterial infections in humans and other animals.

DISCLOSURE OF THE INVENTION

The present inventors made intensive investigations on mycolic acid and its derivatives, cell wall lipid components of the cells of tubercule bacillus and other acid-fast bacteria, and have found that an antibody produced in response to the administration of MGL obtained from these bacterial cells to living bodies recognizes a mycolic acid moiety (namely, mycolic acid itself or a derivative thereof) as an antigen and also recognizes structural differences among the mycolic acid subclasses. The present inventors have also found that an antibody in acid-fast bacterial infection patients recognizes a mycolic acid, mycolic acid salt, mycolic acid ester or an ester of fatty acid having a carbon number of 14 or more other than mycolic acid with a mono- or disaccharide, as an antigen, and that, when using (as a sample) a body fluid of a patient infected with tubercule bacillus or an acid-fast bacterium closely related thereto, the antibody contained therein recognizes the above-mentioned compounds as antigens. The present inventors made further investigations based on these findings, and completed the present invention.

Accordingly, the present invention provides the following 1), 2) and 3):

1) A reagent for detection of an antibody against an acid-fast bacterial antigen to identify acid-fast bacterial species and its detection method.

2) A reagent for detection of an antibody against an acid-fast bacterial antigen to identify acid-fast bacterial genera (including the genera Mycobacterium, Nocardia and Rhodococcus) and its detection method.

3) A method of diagnosis of acid-fast bacterial infections wherein the difference in absorbance between a sample taken from a healthy human and a sample from a subject is determined by a detection method for an antibody against an acid-fast bacterial antigen described in 1) or 2) above.

In the present invention, the acid-fast bacterial genera are mainly Mycobacterium, Nocardia and Rhodococcus, etc. Examples of acid-fast bacterial species belonging to the genera Mycobacterium include tubercule bacilli, such as *M. tuberculosis* and *M. bovis*; and acid-fast bacteria closely related thereto, such as *M. kansasii*, *M. leprae*, *M. intracellulare-M. avium* complex and atypical mycobacteria, such as *M. scrofulaceum* and *M. fortuitum*.

In the scope of the present invention, mycolic acid is defined as a compound having a structure of the following formula (I):

wherein $R^1$ and $R^2$ independently represent a $C_{10-60}$ normal or branched aliphatic chain.

Here, $R^1$ and $R^2$ may have groups with different polarities, e.g., cycloalkyl groups, such as cyclopropane ring; lower alkyl groups, such as methyl group; lower alkoxy groups, such as methoxy group; epoxy group, hydroxy group, carbonyl group and carboxyl group, and may have a double bond (preferably 1 to 7 double bonds).

The structure of the mycolic acid obtained from bacterial cells varies widely among the bacterial species and total carbon number, double bond number and the carbon numbers of $R^1$ and $R^2$ are taxonomically significant. As for total carbon number, it varies very widely; for example, $C_{80}$ or more is often the case with the genus Mycobacterium, $C_{50}$ or so with the genus Nocardia and $C_{30}$ or so with the genus Corynebacterium. In addition, $R^1$ and $R^2$ have various groups with different polarities, such as cyclopropane ring, methyl group, methoxy group, epoxy group, hydroxy group, carbonyl group and carboxyl group. These facts are already known ["*Biseibutu no Kagaku Jikkenho*", published by Gakkai Syuppan Center, 131–143 (Feb. 10, 1985, 3rd printing); European Journal of Biochemistry, 139, 173–180 (1984)].

It should be noted, however, that the difference in substitution is significant in identification of bacterial species in the present invention. For example, the following subclasses are known to be obtained from bacterial cells.

(a) α-mycolic acid ($C_{78}$ <, *M. tuberculosis*)

(b) Methoxy-mycolic acid ($C_{85}$ <, *M. tuberculosis*)

(c) β-mycolic acid (or keto-mycolic acid) ($C_{85}$ <, *M. tuberculosis*)

(d) Dicarboxy-mycolic acid ($C_{60}$ <, *M. phlei*)

Examples also inclulde α'-mycolic acid (the same as α-mycolic acid except for carbon number) and those having an epoxy group.

The mycolic acid involved in the present invention is defined as above, but the carbon numbers shown above are average values, and the mycolic acid may be a mixture of various mycolic acids with different carbon numbers.

In the present invention, the mycolic acid salt means the salt of the mycolic acid defined above with a metal, such as sodium or potassium.

In the present invention, the mycolic acid ester means not only an ester with a mono- or disaccharide but also an alkyl, alkenyl, silyl or aryl ester. These esters are not subject to limitation as long as they do not interfere with the antigen-antibody reaction. Examples of such esters include methyl ester, ethyl ester, t-butyl ester, phenyl ester, trimethylsilyl ester and benzyl ester, etc.

The fatty acid having a carbon number of 14 or more (preferably 14 to 80, more preferably 14 to 40) other than mycolic acid means a saturated or unsaturated aliphatic carboxylic acid which may have a substituent, such as a hydroxyl group, a lower alkoxy group, a lower alkyl group, an epoxy group, a carbonyl group or a carboxyl group. Examples of simple fatty acids having no substituent include saturated fatty acids, such as myristic acid, pentadecanoic acid, palmitic acid, heptadecanoic acid, stearic acid, nonadecanoic acid, arachidic acid, behenic acid, lignoceric acid, cerotic acid, heptacosanoic acid, montanoic acid, melissic acid and vaccenic acid; and unsaturated fatty acids, such as oleic acid, elaidic acid, cetoleic acid, erucic acid, brassidic acid, linoleic acid, linolenic acid, arachidonic acid and stearolic acid.

In the present invention, the monosaccharide means not only a normal, branched or cyclic monosaccharide, such as pentose, hexose, heptose, octose, nonose or decose, but also a substitution product, such as deoxy sugar, methyl sugar, thio sugar or amino sugar.

The disaccharide means maltose, cellobiose, gentiobiose, melibiose, lactose, turanose, sophorose, trehalose, isotrehalose, sucrose or isosaccharose.

In the present invention, the alkyl, alkenyl or aryl is not subject to limitation. Examples thereof include alkyls (e.g. normal, branched or cyclic alkyls, such as methyl, ethyl, propyl, isopropyl, isobutyl, sec-butyl, tert-butyl, butyl, hexyl, cyclohexyl) which may be substituted; alkenyls (e.g. normal, branched or cyclic alkenyls, such as allyl, vinyl, benzyl and styryl); and aryls (e.g. phenyl and naphthyl). Specifically, the lower alkyl in the present invention means an alkyl having a carbon number of 6 or less, such as methyl, ethyl, propyl, isopropyl, isobutyl, sec-butyl, tert-butyl, butyl, n-amyl, isoamyl, hexyl, cyclopentyl and cyclohexyl.

The above-mentioned mycolic acids or mycolic acid esters with a substance other than a saccharide are produced by a method known per se (e.g. extraction and synthesis from bacterial cells).

Extraction from bacterial cells is carried out as follows:

Bacterial cells are subjected to direct hydrolysis and organic solvent extraction, followed by separation by TLC (thin layer chromatography), or glycolipids are extracted and separated from bacterial cells with chloroform-methanol or other solvent, and subjected to hydrolysis, followed by organic solvent extraction of the lipids and TLC separation, to afford the mycolic acids of different subclasses.

These mycolic acids can be further converted to lower alkyl esters, etc. by conventional methods.

These mycolic acids or mycolic acid esters with a substance other than a saccharide (e.g. mycolic acid lower alkyl esters) can also be obtained by synthesis by conventional methods as follows:

In these formulas, $R^3$—$CH_2$ is identical with $R^1$ in the above formula (I) and $R^2$ has the same definition as above.

In accordance with Method A, when producing a branched fatty acid like α-alkyl-β-hydroxy fatty acid (III) [the mycolic acid represented by the above formula (I)], the desired product mycolic acid lower alkyl ester (II) can be obtained by Claisen condensation of the fatty acid ester followed by reduction with $NaBH_4$ as described in literature [Bull. Soc. Chim. Fr., 504–510 (1954)] when $R^3$ and $R^2$ represent the same alkyl group.

In accordance with Method B, the mycolic acid lower alkyl ester (II) can be obtained by condensation of an aliphatic aldehyde and an α-bromocarboxylic acid ester by Reformatsky reaction, when $R^3$ and $R^2$ are alkyl groups different from each other. Hydrolysis of the compound (II) obtained by Method A or B affords the desired product compound (III) [mycolic acid (I)].

In accordance with Method C, the compound (III) [mycolic acid (I)] can be directly obtained by condensation of an aliphatic aldehyde and a carboxylic acid preferably in the presence of a strong base, such as LDA (lithium diisopropylamide) at a concentration of 2 moles or more, when $R^3$ and $R^2$ are alkyl groups different from each other.

Synthesis of course affords various mycolic acids with different desired carbon numbers and with uniform composition.

Note that a mycolic acid salt can be prepared easily, for example, by reaction of a mycolic acid with a base.

A fatty acid having a carbon number of 14 or more other than mycolic acid is also prepared by a method known per se.

The mycolic acid (obtained from bacterial cells or by synthesis), mycolic acid salt or fatty acid having a carbon number of 14 or more thus obtained is esterified with a mono- or disaccharide described above by a known method to yield an ester with a saccharide.

In the present invention, the disaccharide is preferably trehalose. In other words, the ester is preferably an ester of mycolic acid with trehalose or another ester of a fatty acid having a carbon number of 14 or more other than mycolic acid with trehalose (hereinafter abbreviated as TFE).

Examples of TFE include trehalose palmitate, trehalose myristate, trehalose stearate, trehalose octadecadienoate, trehalose corynomycolate and trehalose mycolate, specifically, 6,6'-di-O-palmitoyl-α,α-trehalose, 6,6'-di-O-mycoloyl-α,α-trehalose and 2,6'-di-O-oleoyl-α,α-trehalose.

The TFE includes known compounds and is produced by subjecting trehalose and the above-mentioned mycolic acid (obtained from bacterial cells or by synthesis), mycolic acid salt or fatty acid having a carbon number of 14 or more to an esterification process known per se. For example, a di-substitution product of trehalose at the 6- and 6'-positions can be produced by the method described in Japanese Patent Publication Open to Public Inspection No. 185599/1983 and Chemistry and Physics of Lipids, vol. 27, pp. 345–352 (1980), or a method analogous thereto.

Also, an asymmetric di-substitution product of trehalose (e.g. substituted at the 2- and 6'-positions) can be produced by protecting each of the 4- and 6-positions and 4'- and 6'-positions of trehalose with a protective group, isomerizing them by a known method; again protecting the 6-position; diacylating the 2- and 6'-positions with a desired fatty acid, and deprotecting the protected groups other than those at the 2- and 6'-positions.

The TFE is preferably an ester comprising trehalose bound with 1 to 4 fatty acids (including mycolic acid) at optional positions, preferably at any of the 2-, 2'-, 3-, 3'-, 6- and 6'-positions, with further preference given to an ester comprising trehalose bound with two fatty acids (including mycolic acid) at the 6- and 6'-positions.

In the present invention, it is possible to even identify infecting bacterial species when a mycolic acid ester of each subclass is used as a reagent for the detection of the antibody against an acid-fast bacterial antigen; therefore, the trehalose mycolic acid ester (hereinafter abbreviated as TME) is preferable among the TFEs.

Examples of the TME include trehalose monomycolate, trehalose dimycolate, trehalose trimycolate and trehalose tetramycolate, with preference given to trehalose-6,6'-dimycolate.

Specific examples of the TME include 6'-O-corynomycoloyl-2-O-pentadecanoyl-α,α-trehalose, 2-O-icosahoyl-6'-O-(3-hydroxy-2-n-octadecyl-tetracosanoyl)-α,α-trehalose, 2-O-(9-octadecenoyl)-6'-O-(3-hydroxy-2-tetradecyl-11-icosenoyl)-α,α-trehalose, 2-O-pentadecanoyl-3-O-octadecanoyl-6'-O-(3-hydroxy-2-n-tetradecyl-docosanoyl)-α,α-trehalose, 2,3-di-O-eicosanoyl-6'-O-(3-hydroxy-2-n-octadecyl-tetracosanoyl)-α,α-trehalose and 2,3-di-O-(9-octadecenoyl)-6'-O-(3-hydroxy-2-tetradecyl-11-icosenoyl)-α,α-trehalose.

The TME includes known compounds, and can be extracted and isolated from acid-fast bacteria, such as those of the genera Mycobacterium, Nocardia, Rhodococcus and Corynebacterium by a known method as in the method of the extraction of mycolic acid from bacterial cells described above. In this case, it is possible to obtain trehalose-6-monomycolate, trehalose-6,6'-dimycolate (cord factor), trehalose-2,3,6'-trimycolate, trehalose-2,6,6'-trimycolate and others derived from various bacterial species.

As stated above, it is possible to separate TME directly from bacterial cells on the basis of the number of mycolic acids bound to trehalose but not possible on the basis of the kind (subclass), such as different mycolic acid substituent, etc. For this reason, when a desired mycolic acid derived from bacterial cells is bound to a particular position of trehalose, TME can be produced by extracting, separating and isolating mycolic acid alone from an acid-fast bacterium by a known method and subjecting them and trehalose to the esterification process known per se which has been described above.

In the present invention, it is also possible as in the case of disaccharides, to produce an ester of a mycolic acid (produced from bacterial cells or by synthesis), a mycolic acid salt or a fatty acid having a carbon number of 14 or more with a monosaccharide.

In the detection of the antibody against the acid-fast bacterial antigen, identification of acid-fast bacterial species, identification of acid-fast bacterial genera (including Mycobacterium, Nocardia and Rhodococcus) or diagnosis of acid-fast bacterial infections using the reagent of the present invention, it is preferable that the mycolic acid, mycolic acid salt, mycolic acid ester (hereinafter abbreviated as MS) or the ester of fatty acid having a carbon number of 14 or more other than mycolic acid with a mono- or disaccharide (hereinafter abbreviated as SFE) be used after being immobilized on a plate. These antigens are then brought into contact with an antibody-containing sample (e.g. body fluid, particularly blood, serum, plasma, pleural effusion, ascites fluid or urine of a patient infected with tubercule bacillus) and analyzed by the ELISA (enzyme-linked immunosorbent assay) method, a method known per se.

Thus, two methods are available for the detection; the one-step assay method and the two-step assay method. In the one-step assay method, a solid phase prepared by immobilizing various kinds of MS or SFE onto wells, etc., a sample, and an enzyme-labeled antibody are reacted at the same time. After a given length of time, the unreacted portion of the labeled antibody is removed by washing, followed by determination of the enzyme activity of the solid phase to identify the antibody contained in the sample according to the MS or SFE.

In the two-step assay method, an immobilized antigen and a sample are reacted. After a given length of time, the unreacted portion of the antibody in the sample is removed by washing, followed by reaction with an enzyme-labeled antiantibody. After a given length of time, the unreacted portion of the labeled antibody is removed by washing, followed by determination of the enzyme activity of the solid phase to identify the antibody contained in the sample according to the MS or SFE. For further identification in more detail, that is, identification of acid-fast bacterial species, MS separated for each subclass is immobilized onto wells.

The method of immobilization is not subject to limitation as long as the object of the present invention is not interfered with. For example, MS or SFE is dissolved in an organic solvent, such as hexane, isopropanol or ethanol, and the resulting solution is added to wells of a microplate, etc., to immobilize the MS or SFE. Immobilization is achieved in about 2 to 48 hours. It is preferable to wash the wells with an appropriate solvent and block it after immobilization.

The reaction of MS or SFE in the wells and the antibody in the sample is carried out under the condition in which the reaction proceeds easily (e.g. in a humid box at a temperature of 20° to 40° C. and a humidity of 70 to 100%) for about 30 minutes to 2 hours until it completes itself. After completion of the reaction, an antiantibody is added with or without removal of the unreacted substances in the wells and the reaction is carried out in the state in which the reaction proceeds easily (e.g. in a humid box at a temperature of 20° to 40° C. and a humidity of 70 to 100%) for about 10 minutes to 2 hours until it completes itself. The reaction residue is removed and the wells are washed with an organic solvent such as hexane or isopropanol, a phosphate buffer or another washing agent.

The above-mentioned antiantibody is an antiantibody against the above-mentioned primary antibody and is prepared using an animal (no limitation is posed on the animal species; examples of usable animals include goats, horses, sheep and bovines). It is preferable to use an antiantibody against IgM (IgG may be included) when using a mycolic acid, mycolic acid salt or mycolic acid ester of each subclass to identify bacterial species, and to use an antiantibody against IgM+IgG when using an ester of a fatty acid having a carbon number of 14 or more other than mycolic acid with a saccharide (mono- or disaccharide) to identify bacterial genera. In the present invention, an antiantibody coupled with a marker is used. Here, any substance normally used for immunoassay can be used as a marker, and examples of such substances include enzymes, radioactive substances, luminescent substances and fluorescent substances. Examples of enzymes include peroxidase, β-D-galactosidase and alkaline phosphatase. Examples of radioactive substances include iodine and deuterium. Examples of luminescent substances include acrydium salts. Examples of fluorescent substances include fluorescein isothiocyanate.

The purpose of producing an antiantibody coupled with a marker can be fully accomplished by a method known per se.

Then, the antiantibody involved in the reaction is assayed as follows: When the antiantibody is coupled with, for example, peroxidase as a marker, the peroxidase is reacted with o-phenylenediamine and hydrogen peroxide to cause color development, followed by optical density (OD) determination at a main wavelength of 492 nm and a subwavelength of 690 nm.

It is desirable that the results be calculated as differences in optical density difference (ODD) between the average OD of a healthy human as control and the OD of the sample. When ODD is not less than 0.100, it indicates the presence of a significant level of an antibody produced by an acid-fast bacterium, and thus the subject from which the sample was collected (including non-human animals) is judged as being infected with an acid-fast bacterium (tubercule bacillus or an acid-fast bacterium closely related thereto).

The samples are body fluids of animals including humans. Examples of non-human animals include mammals, such as horses, swines and chickens, and birds. Examples of usable body fluids include serum, plasma, cerebrospinal fluid, saliva, pleural effusion, ascites fluid and urine. In the present invention, the sample can be prepared in accordance with a known method. When assaying the antibody in, for example, serum, it is preferable to use the serum in dilution at 40 to 640 folds, ideally 160 folds.

The reagent for the detection of the antibody against an acid-fast bacterial antigen of the present invention, the method of the detection of the antibody against an acid-fast bacterial antigen using said reagent, and the method of the diagnosis of acid-fast bacterial infections based on said detection method are simpler in procedures and offer much higher specificity, in comparison with conventional reagents and methods.

Particularly, the reagent of the present invention allows very quick antibody detection, bacterial identification and infection diagnosis since an assay is conducted by directly using a body fluid of patients with an acid-fast bacterial infection as a sample based on the ELISA method.

Furthermore, since reagents used for the present invention (MS and SFE) can also be produced by synthesis, they can be easily supplied in large amounts on an industrial scale.

In addition, the reagent and the method of the present invention permit high sensitive assay, enabling the assay of a trace amount of antibody present in serum.

Thus, simple and quick detection of the antibody against an acid-fast bacterial antigen can be conducted using the reagent by the method of the present invention and in turn identification of acid-fast bacterial genera (including the genera Mycobacterium, Nocardia and Rhodococcus) can be performed. According to the present invention, a diagnosis to identify the infecting acid-fast bacterium is made on the basis of acid-fast bacterial species identification using a mycolic acid, mycolic acid salt or mycolic acid ester (MS) of each subclass as a reagent for the detection of an antibody against an acid-fast bacterial antigen, thereby resulting in particular effect that quick choice of therapeutic drug for the disease is possible.

BEST MODE OF CARRYING OUT THE INVENTION

The present invention is hereinafter described in more detail by means of the following examples, but the invention is not by any means limited by them.

Note that in Examples 1 through 10, assays were made by the ELISA procedure described below, with serum dilution rates of 5, 10, 20, 40 and 80 folds in Examples 1 through 6. The results are shown in respective figures.

Assay by ELISA

An ethanol or isopropanol solution of the antigen is dispensed to a 96-well microplate at 50 µl/well. This microplate is then kept standing overnight to evaporate the solution to dryness to adsorb the antigen.

To this microplate is added 100 µl/well of a phosphate buffered saline (pH 7.4) supplemented with 0.5% Tween 20 (hereinafter abbreviated as PBS-T), and the microplate is kept standing at room temperature for 10 minutes. Otherwise, 100 µl/well of PBS-T supplemented with 5% bovine serum albumin is added, and the microplate is kept standing at room temperature for 2 hours.

After the PBS-T or the PBS-T supplemented with 5% bovine serum albumin is removed by suction, 50 µl/well of the antibody (serial dilution of serum) is dispensed, and the microplate is kept standing at room temperature for 1 hour.

After 3 times of washing with PBS-T, 50 µg/well of peroxidase-labeled antimouse Ig(G+M) was added, and the microplate is kept standing at room temperature for 1 hour.

After 3 times of washing with PBS-T, 50 µl/well of citrate buffer supplemented with both o-phenylenediamine and aqueous hydrogen peroxide (pH 4.9) is dispensed, followed by addition of 50 µl/well of 6N HCl and determination of optical density at 492 nm using a microplate reader.

EXAMPLE 1

Detection of antibodies against Nr-TDM, GM and MM by the ELISA method

Antigens: Trehalose-dimycolate (hereinafter abbreviated as TDM), glucose-monomycolate (hereinafter abbreviated as GM) and mannose-monomycolate (hereinafter abbreviated as MM), all derived from *Nocardia rubra* (hereinafter abbreviated as Nr-), were each prepared as a 200 µg/ml ethanol solution. Each solution was dispensed to a 96-well microplate at 10 µg/50 µl/well, and the microplate was kept standing overnight to evaporate the solution to dryness for antigen adsorption. The results for these antigens are respectively represented by TDM, GM and MM in FIG. 1.

Antibodies: ICR mice were dosed with Nr-derived (Nr-) TDM, GM or MM in the form of a water-in-oil-in-water type emulsion (hereinafter abbreviated as w/o/w emulsion) containing 3.2% Freund's incomplete adjuvant at a dose of 30 µg/mouse by intravenous injection via tail vein (hereinafter abbreviated as i.v.) 10 times every other day. Two days after the final administration, blood was collected. The serum thus obtained was 5-fold diluted with PBS-T, after which it was thermally treated at 56° C. for 30 minutes to inactivate the complements in the serum (hereinafter referred to as inactivation) to yield an original solution, which was then used in serial dilutions with PBS-T. The results for these antibodies are respectively represented by TDM, GM and MM in FIG. 1.

Results

Figure 1:
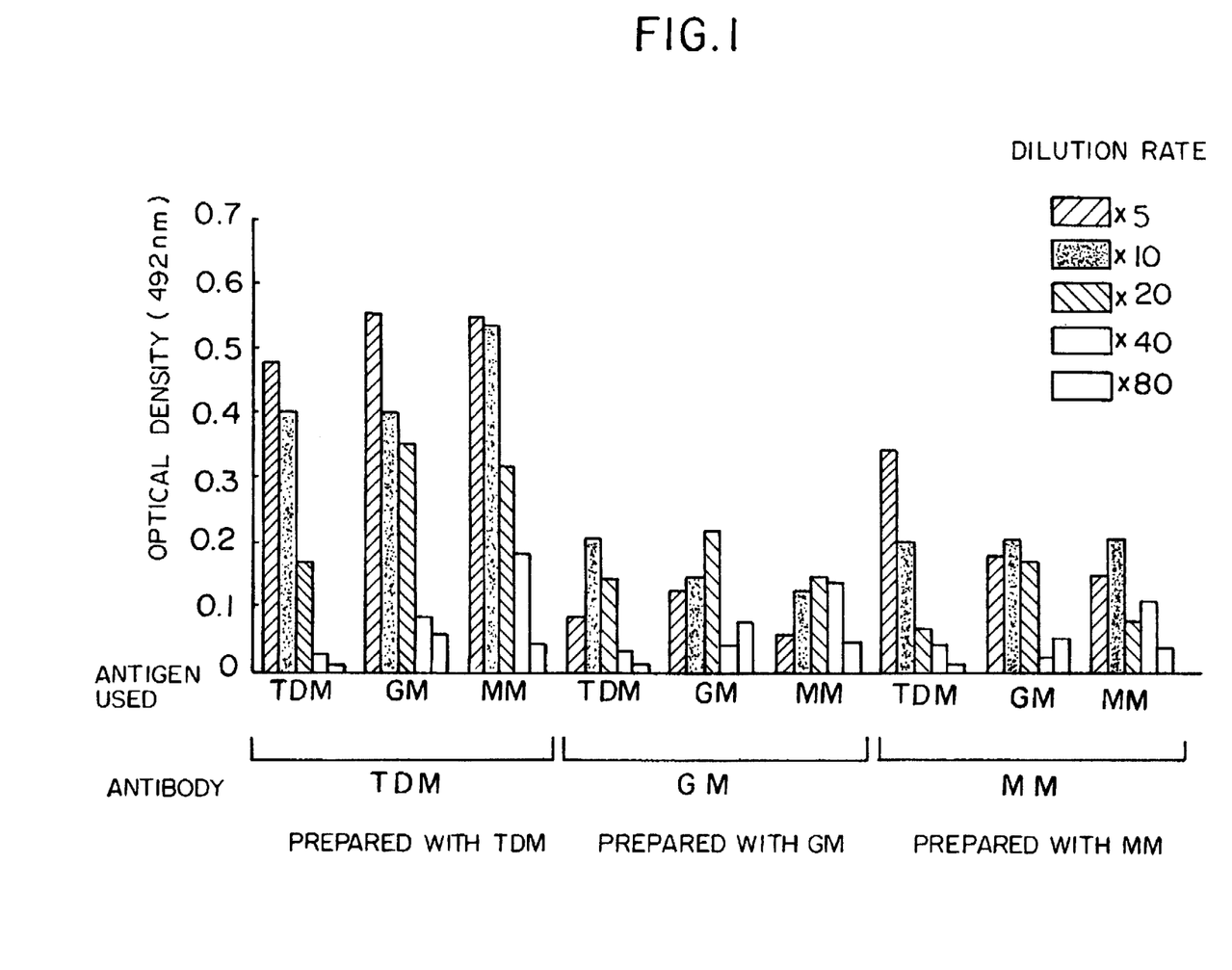
FIG. 1 is a graph showing the detection of the antibodies against trehalose-dimycolate (TDM), glucose-monomycolate (GM) and mannose-monomycolate (MM), all derived from *Nocardia rubra* (Nr-) by the ELISA method.

As shown in FIG. 1, the following results were obtained:

1. An antibody which recognizes MGL as an antigen was detected in the serum of mice dosed with MGL (mycolic acid-containing glycolipid) 30 µg×10 times i.v..

2. The serum of TDM-administered mice showed high antibody titer against all of TDM, GM and MM.

EXAMPLE 2

Purposes

1. To examine non-specific adsorption of mouse serum globulin by the antigen Nr-TDM adsorbed to a plate, a serum from the w/o/w control group (described later) was used as an antibody.

2. To determine whether or not the reaction of the antigen glycolipid with mouse serum immunoglobulin is against a nonspecific lipid, egg yolk phosphatidylcholine (PC) was used as an antigen.

3. The effects of blocking procedure using 5% bovine serum albumin (BSA) to the antigen-adsorbed plate were evaluated.

Antigens: Nr-TDM or PC was prepared as a 200 µg/ml ethanol solution. Each solution was dispensed to a 96-well microplate at 10 µg/50 µl/well. This microplate was kept standing overnight to evaporate the solution to dryness for antigen adsorption.

Figure 2:
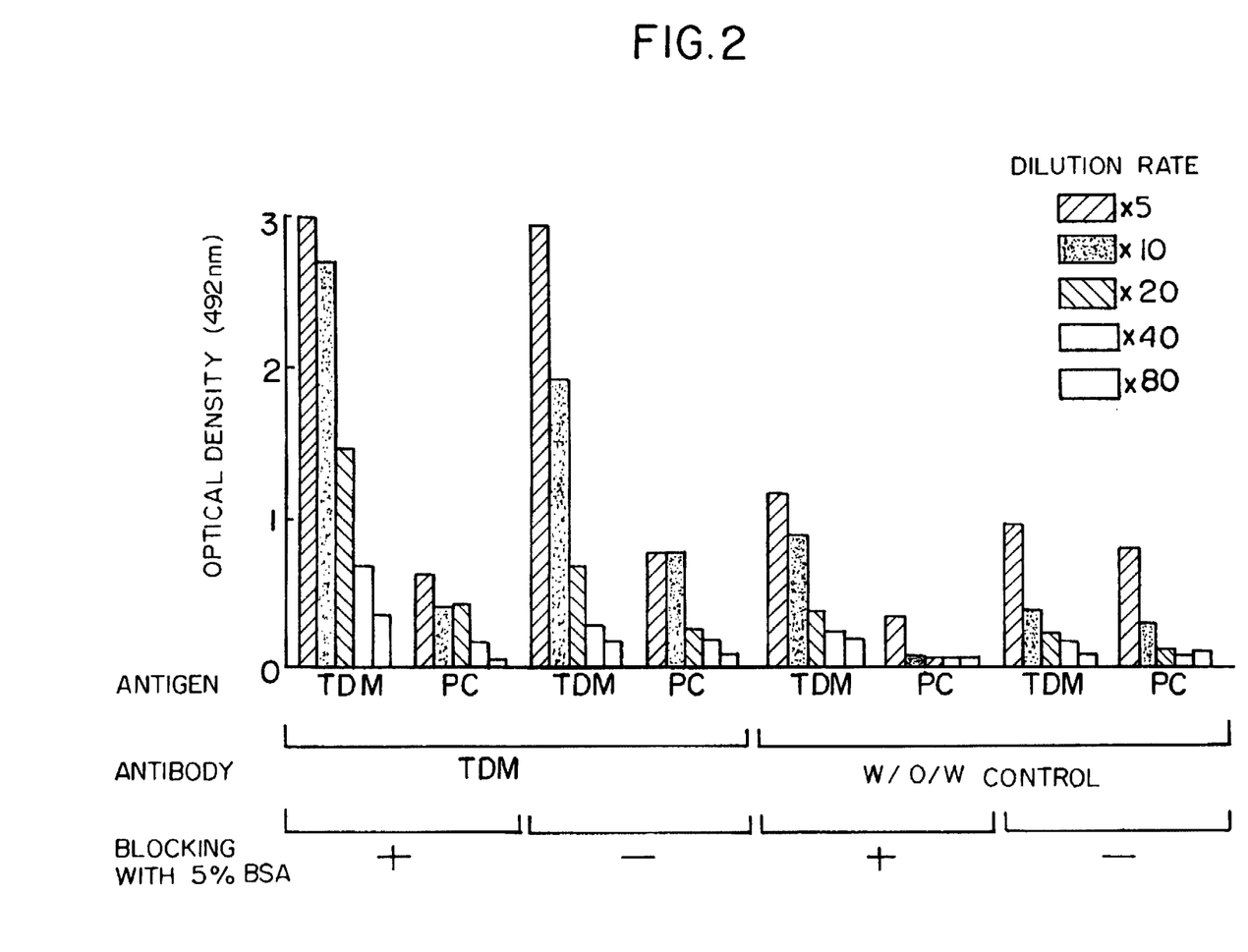
FIG. 2 is a graph showing the detection of the antibody against Nr-TDM by the ELISA method.

The results for these antigens are respectively represented by TDM and PC in FIG. 2.

Antibodies 1) 5-fold dilution of a serum obtained from ICR mice dosed with Nr-TDM 30 µg×10 times (the same as in Example 1).

2) Inactivated 5-fold dilution with PBS-T of a serum obtained by blood sampling from ICR mice dosed with 0.2 ml/mouse of a w/o/w emulsion containing no glycolipid 10 times every other day. The results for these antibodies are respectively represented by TDM and w/o/w control in FIG. 2.

Results

As shown in FIG. 2, the following results were obtained:

1. Almost no reaction took place between the antigen (TDM or PC) and the serum of the w/o/w control group; it was confirmed that the adsorption was not non-specific.

2. No reaction took place between the antigen PC and the antibody of the TDM group; it was confirmed that the reaction was not a reaction with a non-specific lipid.

3. The blocking procedure with 5% BSA had no particular effects.

EXAMPLE 3

Examination of differences in antibody titer against Nr-TDM by the mouse immunization method Antigen: Nr-TDM was prepared into a 200 µg/ml ethanol solution. This solution was dispensed to a 96-well microplate at 10 µg/50 µl/well, followed by antigen adsorption.

Antibodies 1) 5-Fold dilution of a serum obtained from ICR mice dosed with Nr-TDM 30 µg×10 times (the same as in Example 1).

2) 5-Fold dilutions of sera obtained by blood sampling from ICR mice at 1, 4, 7 and 14 days following administration of Nr-TDM 300 µg×1 time.

3) 5-Fold dilution of a serum obtained from ICR mice 1 day after administration of 0.2 ml/i.v. of a w/o/w emulsion containing no glycolipid.

Results

Figure 3:
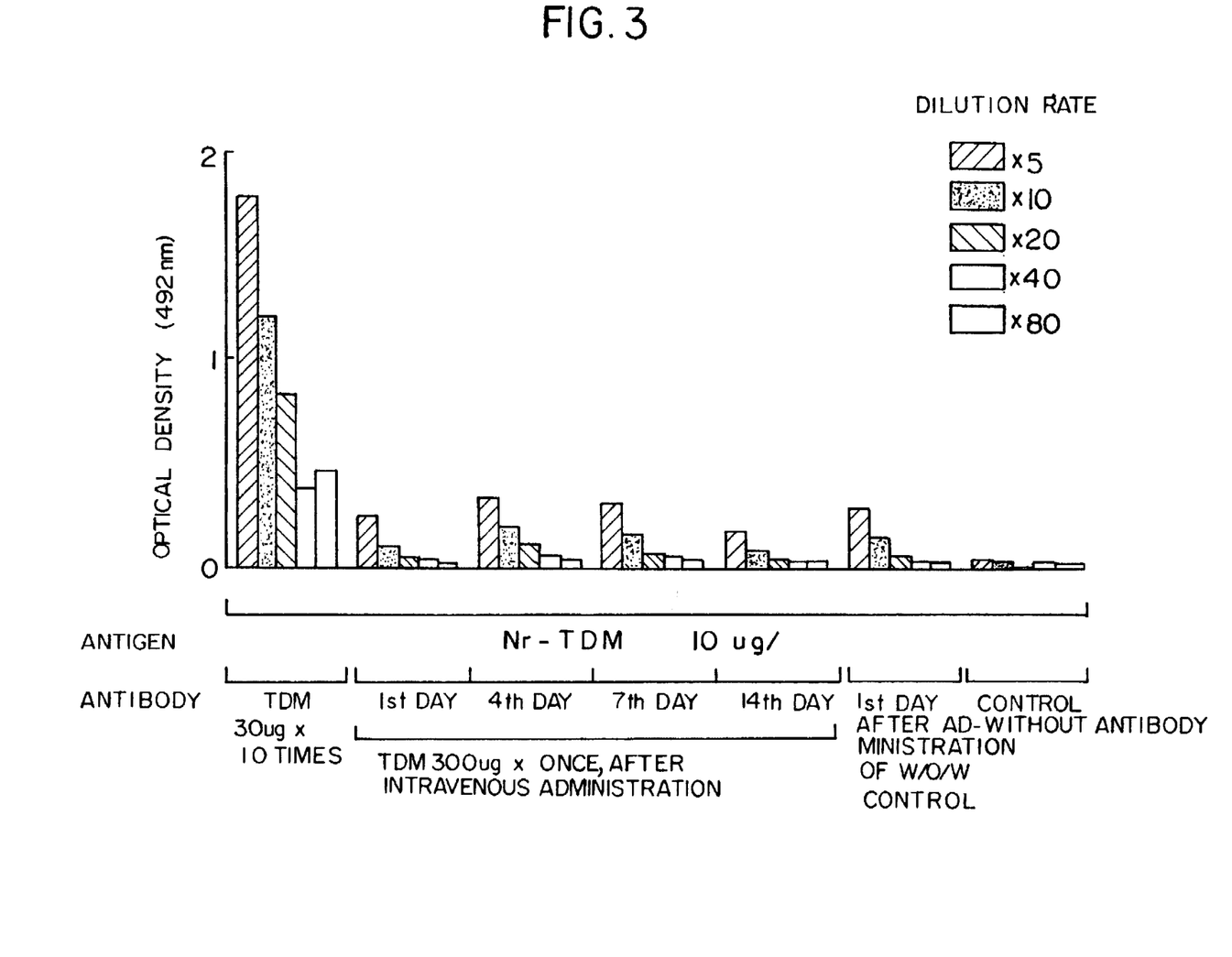
FIG. 3 is a graph showing differences in antibody titer against Nr-TDM determined by the mouse immunization method.

As shown in FIG. 3, the following results were obtained:

1. The same absorbance at 492 nm as in the w/o/w control group was obtained at 1 through 14 days following administration of Nr-TDM 300 µg×1 time; no antibody was detected.

2. Almost no fluorescent coloring occurred in the wells not supplemented with mouse serum; it was confirmed that Nr-TDM showed no non-specific adsorption of the secondary antibody [peroxidase-labeled antimouse Ig(G+M)].

EXAMPLE 4

Examination of reactions when using as antigens Nr bacterial cells with and without mycolic acid removal Antigens 1) Nr bacterial cells.

2) Nr bacterial cells were mixed with a 2:1 (v/v) mixture of chloroform and methanol, followed by ultrasonication to remove the extractable lipid and then acid hydrolysis (see Note 1) to remove the bound lipid (BL).

These antigens 1) and 2) were each suspended in a borate buffer so that the absorbance at 525 nm became 0.43. Each original suspension thus obtained was diluted at 1/1, 1/5 and 1/25 fold dilution rates. Each dilution thus obtained was dispensed to a plate at 50 µl/well. This plate was kept standing overnight for antigen adsorption, followed by supernatant removal by suction.

Antibodies

1) Serum collected from ICR mice dosed with Nr-TDM 30 µg×10 times (the same as in Example 1).

2) Serum collected from ICR mice dosed with w/o/w control 0.2 ml×10 times (the same as in Example 2).

Results

Figure 4:
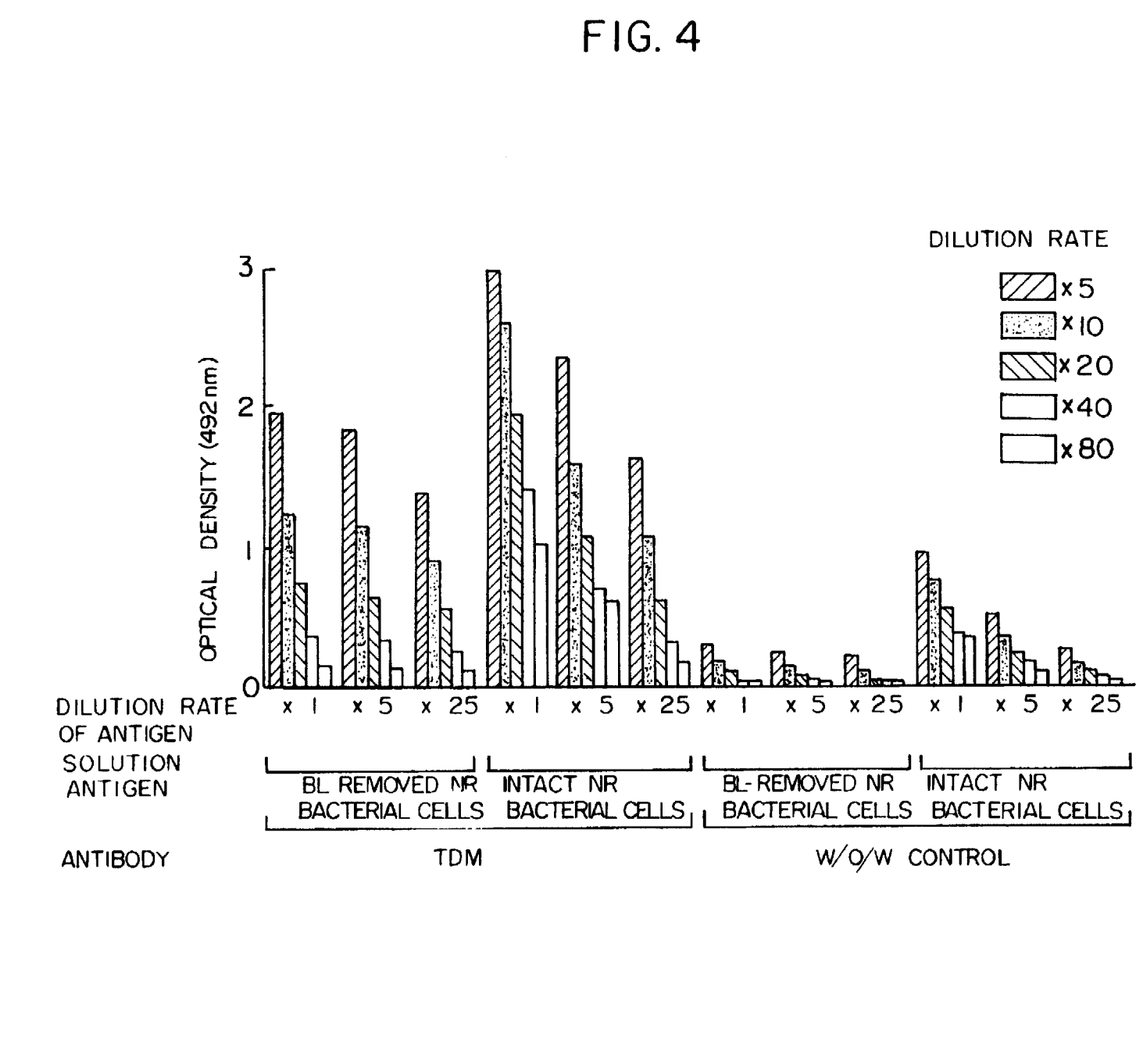
FIG. 4 is a graph showing the reactions using as antigens Nr bacterial cells with and without the mycolic acid removal.

As shown in FIG. 4, the following results were obtained:

1. The Nr bacterial cells reacted with the antibody.

2. The reactivity to the antibody decreased in response to removal of the lipid (mycolic acid) from the Nr bacterial cells.

(Note 1): Acid hydrolysis: After addition of 6N HCl in an amount of about one-third of the cell suspension, the cell suspension was heated at 90° C. overnight, followed by lipid extraction with n-hexane. The resulting water layer was used as antigen.

EXAMPLE 5

Examination of the antigenicity of mycolic acid lower alkyl ester

Antigens

1) Nr-TDM.

2) Mycolic acid methyl ester obtained by hydrolysis and methylation of Nr-TDM.

These antigens 1) and 2) were each prepared into a 200 µg/ml ethanol solution. Each solution was dispensed to a 96-well microplate at 10 µg/50 µl/well, followed by antigen adsorption.

Antibodies

1) Serum of ICR mice dosed with Nr-TDM 30 µg×10 times (the same as in Example 1).

2) Serum of ICR mice dosed with w/o/w control 0.2 ml×10 times (the same as in Example 2).

Results

Figure 5:
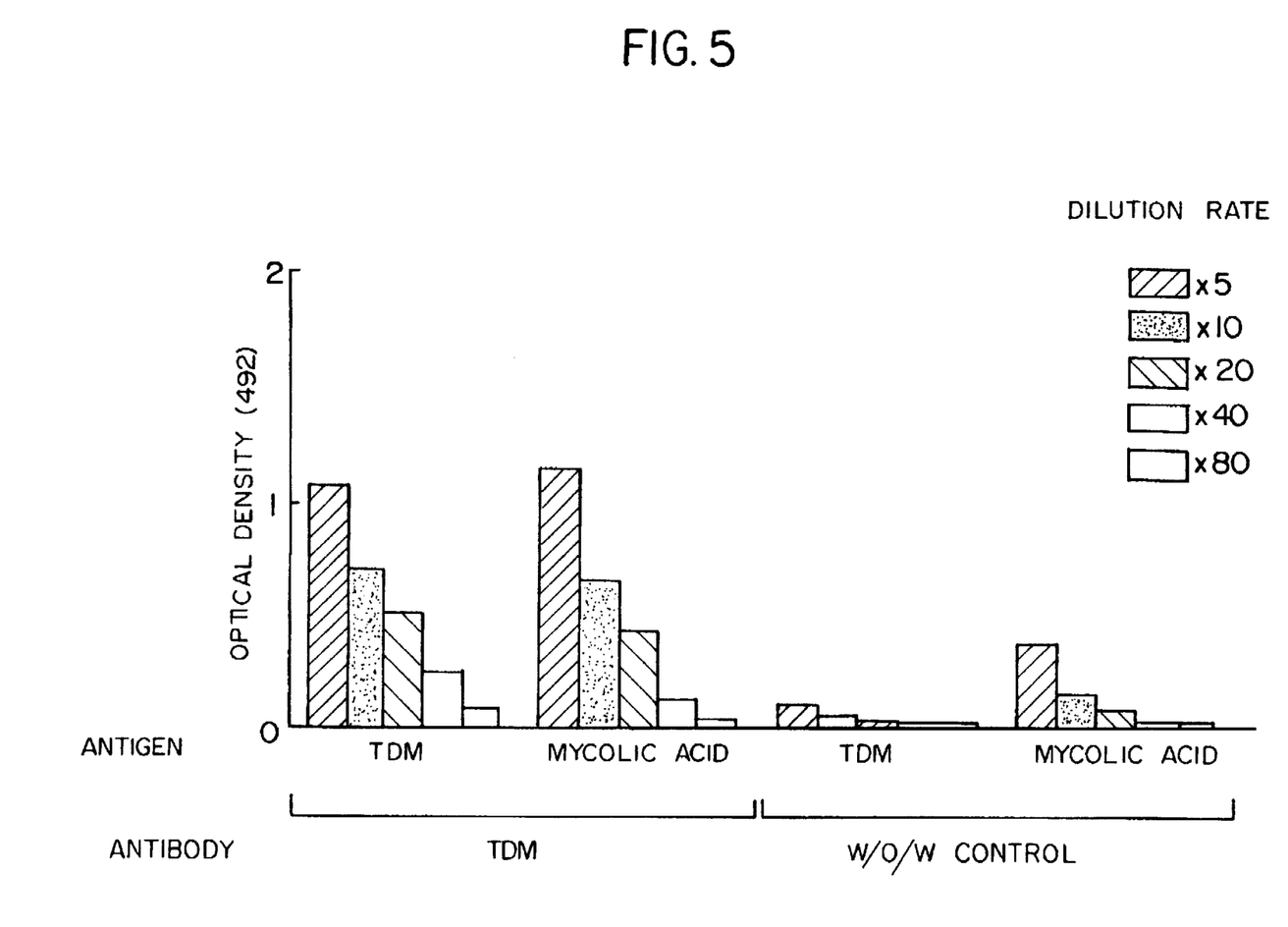
FIG. 5 is a graph showing the antigenicities of mycolic acid methyl esters.

As shown in FIG. 5, the following results were obtained:

The mycolic acid lower alkyl ester showed an antigenicity equivalent to that of TDM.

EXAMPLE 6

Antigens

1) Nr-TDM.

2) *M. intracellulare* [hereiniafter referred to as M. int.]-TDM.

3) *M. kansaii* [hereinafter referred to as M. kan.]-TDM.

4) Nr-derived mycolic acid methyl ester.

5) M. int.-derived α-mycolic acid ($M_1$) methyl ester.

6) M. int.-derived keto-mycolic acid ($M_2$) methyl ester.

7) M. int.-derived dicarboxy-mycolic acid ($M_3$) methyl ester.

Each antigen was prepared into a 200 µg/ml ethanol solution. Each solution was dispensed to a 96-well microplate at 10 µg/50 µl/well. The microplate was kept standing overnight to evaporate the solution to dryness for antigen adsorption.

Figure 6:
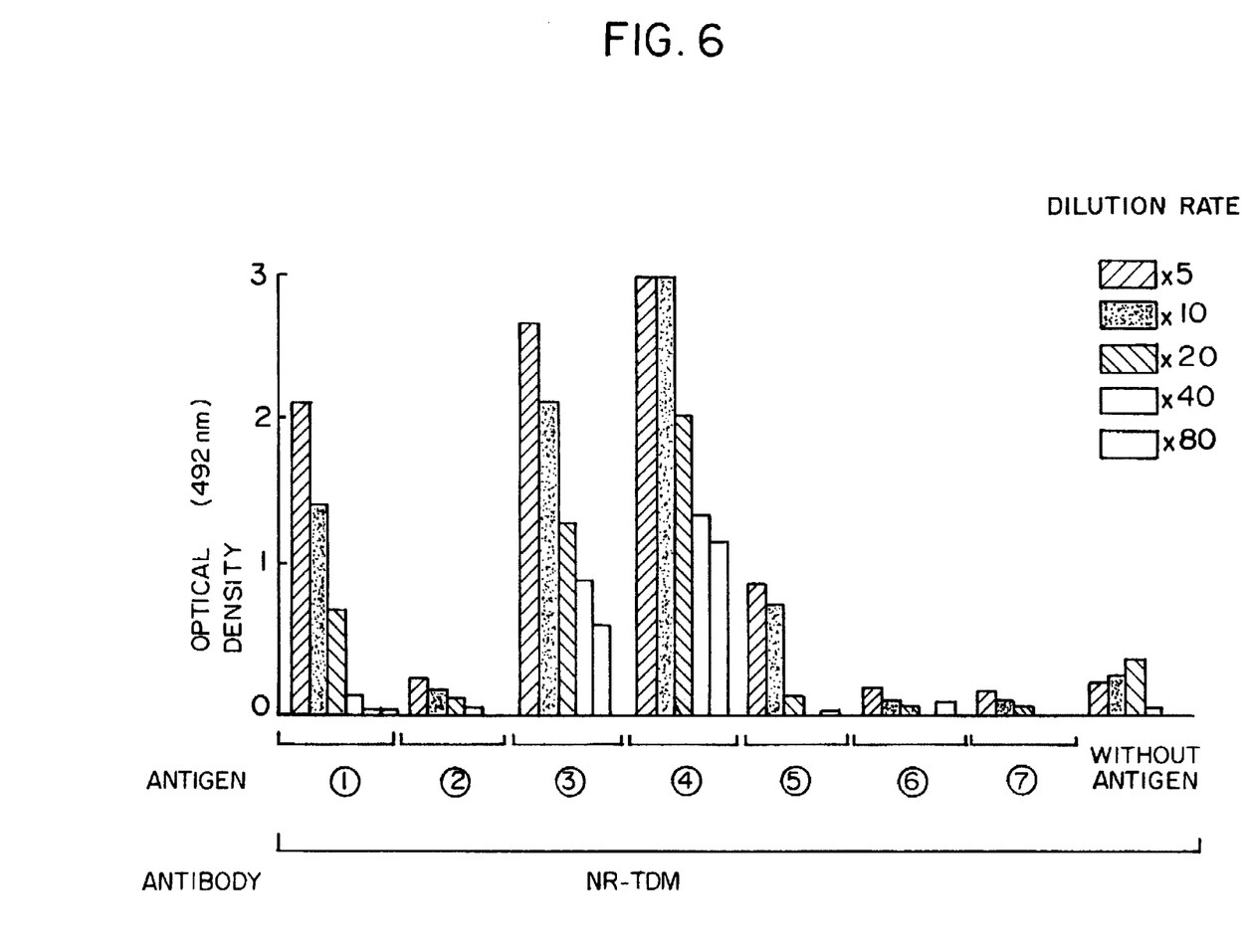
FIG. 6 is a graph showing the reactivities obtained using as antigen various TDMs and mycolic acid methyl esters.

The results for these antigens are respectively represented by 1) through 7) in FIG. 6.

Antibody: 1) Serum of ICR mice dosed with Nr-TDM 30 µg×10 times (the same as in Example 1).
Reference 1. All Nr-derived mycolic acids are α-mycolic acids having a total carbon chain length of $C_{36-48}$ (average 44) and a relatively short side chain of $C_{10-14}$ at the α-position.

2. M. int. has three kinds of mycolic acid which respectively have an average carbon chain length as follows:

| | |
|---|---|
| $M_1$: α-mycolic acid | $C_{80}$ |
| $M_2$: Keto-mycolic acid | $C_{85}$ |
| $M_3$: Dicarboxy-mycolic acid | $C_{69}$ |

3. M. kan. has three kinds of mycolic acid, with the predominance of α-mycolic acid. The average carbon chain length is as follows:

| | |
|---|---|
| α-mycolic acid | $C_{80}$ |
| Methoxy-mycolic acid | $C_{78}$ |
| Keto-mycolic acid | $C_{83}$ |

Results

As shown in FIG. 6, the following results were obtained:

1. The antibody against Nr-TDM reacted with the Nr-TDM, Nr-derived mycolic acid (α-mycolic acid) methyl ester, M. kan.-TDM (most percentage of the mycolic acid is α-mycolic acid) and M. int.-derived α-mycolic acid ($M_1$) methyl ester, but did not react with the M. int.-derived keto-mycolic acid ($M_2$) methyl ester or M. int.-derived dicarboxy-mycolic acid ($M_3$) methyl ester.

2. M. kan.-derived and M. int.-derived mycolic acid methyl esters were almost equivalent to each other in carbon chain length, but were different from each other in subclass composition.

3. Based on these findings, the antiserum of mice immunized with Nr-TDM is considered highly specific to Nr-derived α-mycolic acid esters.

EXAMPLE 7

Nr-TDM was subjected to acid hydrolysis in accordance with the methods of Examples 4 and 5 to yield a vinyl ester and phenyl ester thereof, which were used as antigens.

Antigens

1) Nr-derived mycolic acid vinyl ester.

2) Nr-derived mycolic acid phenyl ester.

3) α-mycolic acid (synthesized product).

4) α-mycolic acid methyl ester (synthesized product).

Each antigen was prepared into a 200 µg/ml ethanol solution. Each solution was dispensed to a 96-well microplate at 10 µg/50 µl/well. This microplate was kept standing overnight to evaporate the solution to dryness for antigen adsorption.

Antibody: Serum of mice dosed with Nr-TDM 30 µg×10 times (the same as in Example 1).
Results 1. The antibody against Nr-TDM reacted with the Nr-derived mycolic acid (α-mycolic acid) vinyl ester and phenyl ester, and also with the α-mycolic acid prepared by organic synthesis and its methyl ester.

2. As stated above, the antiserum collected from mice immunized with Nr-TDM is considered highly specific not only to Nr-derived but also to synthesized α-mycolic acid and its esters.

EXAMPLE 8

M. int.-TDM was subjected to acid hydrolysis in accordance with the method of Example 4, followed by isolation and purification of $M_2$ and $M_3$. A glucose ester of $M_2$ and an arabinose ester of $M_3$ were each prepared and used as antigens.

Antigens

1) M. int.-derived keto-mycolic acid ($M_2$) glucose ester.

2) M. int.-derived dicarboxy-mycolic acid ($M_3$) arabinose ester.

3) Nr-TDM.

4) M. kan.-TDM.

Each antigen was prepared in a 200 µg/ml ethanol solution. Each solution was dispensed to a 96-well microplate at 10 µg/50 µl/well. This microplate was kept standing overnight to evaporate the solution to dryness for antigen adsorption.

Antibody: Serum of mice dosed with M. int.-TDM 30 µg×10 times (prepared in the same manner as in Example 1).
Results 1. The antibody against M. int.-TDM reacted with the $M_2$ glucose ester and $M_3$ arabinose ester but showed a lower reactivity with Nr-TDM and M. kan.-TDM.

2. Based on these findings, it is considered that the antiserum of mice immunized with M. int.-TDM shows high specificity to keto-mycolic acid ester and dicarboxyl-mycolic acid ester, and its reaction response depends not on saccharides but on fatty acids (keto- and dicarboxy-mycolic acids).

EXAMPLE 9

Antigens

1) Trehalose-6,6'-dipalmitate (hereinafter abbreviated as TDP).

2) Hexane (control).

3) Methyl stearate (comparison).

Each antigen was prepared into a 200 µg/ml ethanol solution. Each solution was dispensed to a 96-well microplate at 10 µg/50 µl/well. This microplate was kept standing overnight to evaporate the solution to dryness for antigen adsorption. The results of detection obtained from these antigens are respectively represented by TDP, Control and Stearate in FIG. 7.

Figure 7:
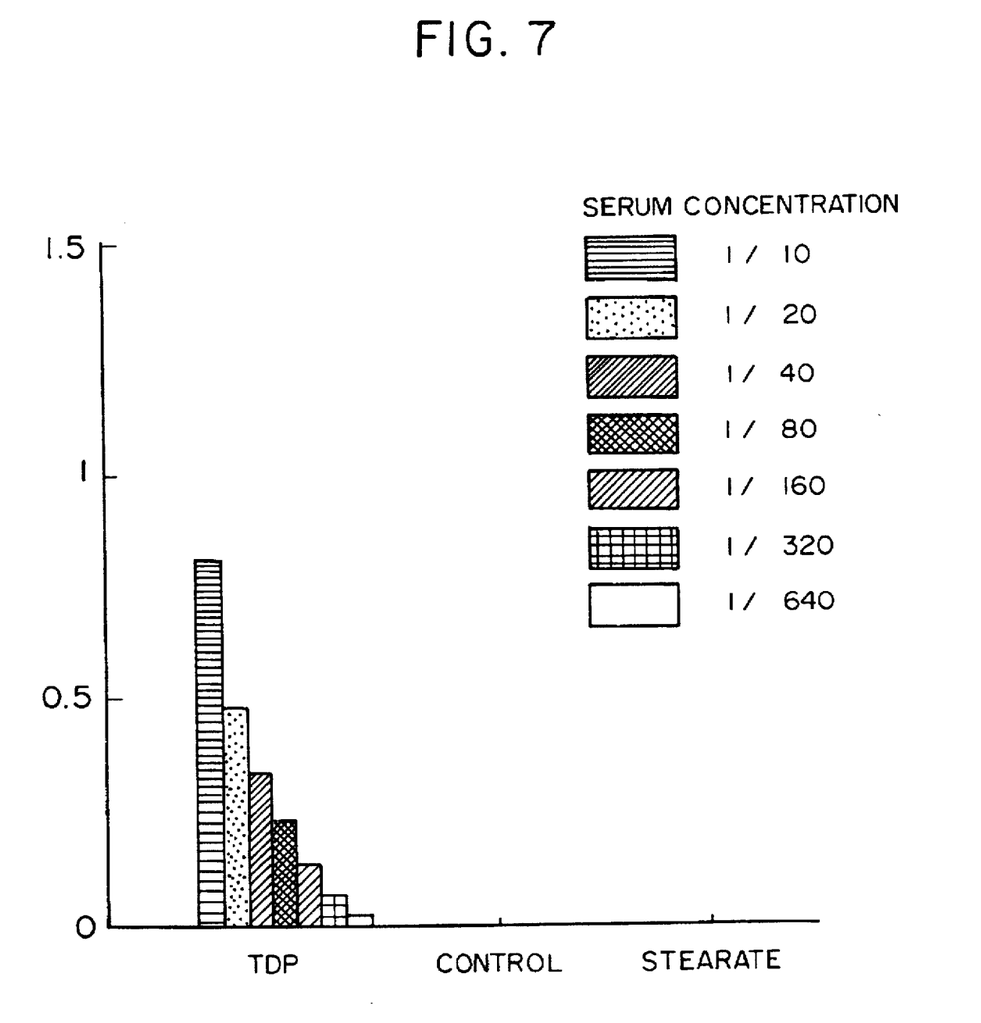
FIG. 7 is a graph showing the detection of antibody by the ELISA method with trehalose-6,6'-dipalmitate (TDP) as an antigen.

Antibody: A serum collected by blood sampling from patients infected with tubercule bacillus who tested positive in bacterial detection was 5-fold diluted with PBS-T and inactivated (heat treated at 56° C. for 30 minutes) to yield an original solution, which was then used in serial dilutions with PBS-T.
Results As shown in FIG. 7, the following results were obtained:

1. The serum of patients infected with tubercule bacillus specifically recognized TDP as an antigen.

2. The serum of patients infected with tubercule bacillus showed a high antibody titer against TDP as well.

Note that when a serum obtained by blood sampling from a healthy human was assayed by the ELISA method in the same manner as above, no color development occurred.

EXAMPLE 10

The procedure of Example 9 was followed except that TDP was changed to the compounds shown below.

1) M. tuberculosis-derived GM and MM (α-, methoxy- or keto-mycolic acids).

2) M. int.-derived α-mycolic acid ($M_1$) or keto-mycolic acid ($M_2$) methyl, vinyl or phenyl ester.

3) M. kan.-derived TDM, GM and MM (α-, methoxy- or keto-mycolic acids).

4) 6-O-palmitoyl-glucose (synthetic monoester).

5) 6-O-palmitoyl-mannose (synthetic monoester).

6) 6,6'-di-O-corynomycoloyl-α,α-trehalose [synthetic TFE (diester)].

7) 6,6'-di-O-palmitoyl-α,α-trehalose [synthetic TFE (diester)].

8) 6,6'-di-O-mycoloyl-α,α-trehalose [synthetic TFE (diester)].

9) 2,6'-di-O-oleoyl-α,α-trehalose [synthetic TFE (diester)].

10) 6'-O-corynomycoloyl-2-O-pentadecanoyl-α,α-trehalose [synthetic TFE (diester)].

11) 2-O-icosanoyl-6'-O-(3-hydroxy-2-n-octadecyl-tetracosanoyl)-α,α-trehalose [synthetic TFE (diester)].

12) 2-O-(9-octadecenoyl)-6'-O-(3-hydroxy-2-tetradecyl-11-icosenoyl)-α,α-trehalose [synthetic TFE (diester)].

13) 2-O-pentadecanoyl-3-O-octadecanoyl-6'-O-(3-hydroxy-2-n-tetradecyl-docosanoyl)-α,α-trehalose [synthetic TFE (triester)].

14) 2,3-di-O-eicosanoyl-6'-O-(3-hydroxy-2-n-octadecyl-tetracosanoyl)-α,α-trehalose [synthetic TFE (triester)].

15) 2,3-di-O-(9-octadecenoyl)-6'-O-(3-hydroxy-2-tetradecyl-11-icosenoyl)-α,α-trehalose [synthetic TFE (triester)].

Results

The serum of patients infected with tubercule bacillus specifically recognized not only TFE but also esters of fatty acids other than mycolic acid with a mono- or disaccharide and mycolic acid esters.

EXAMPLE 11

Method of identifying the genus Mycobacterium and method of diagnosis of acid-fast bacterial infections using samples collected from patients infected with acid-fast bacteria and healthy humans Preparation of glycolipid from bacterial cells

*M. tuberculosis* H37Rv. strain was used as the starting material for cord factor antigen.

Isolation and purification of cord factor antigen

Bacterial cells were suspended in a mixture of chloroform and methanol (2:1, v/v), followed by cell disruption by ultrasonication. The extract from the chloroform layer was evaporated to dryness and dissolved in a small amount of a mixture of chloroform and methanol (2:1, v/v). These extracts were subjected to silica gel TLC using chloroform-methanol-acetone-acetic acid (90:10:6:1, v/v) as a developing solvent. Several bands appeared, out of which trehalose-6,6'-dimycolate (TDM) was separated and recovered using a mixture of chloroform and methanol (2:1, v/v).

Samples

Sera collected from 50 patients infected with an acid-fast bacterium and 55 healthy humans were used as samples.

Healthy humans: All but one were positive in tuberculin dermal reaction.

Patients: All patients were confirmed bacteriologically positive in an acid-fast bacteria detection test by both smear examination and culture. A niacin test revealed that, of the 50 patients, 45 were patients of *M. tuberculosis* (tuberculosis) infection and the other 5 were patients of atypical mycobacterial infection. All patients had a pulmonary disease, of whom 1 had a complication of pleurisy and 7 had a complication of diabetes mellitus. The patients were aged in the range of 20 to 80. The blood samples were collected after special chemotherapy in 46 patients and before the treatment in 4 patients.

Also separately tested were sera of patients not infected with acid-fast bacterium and having a cancer (adenocarcinoma) in one lung.

Assay by the ELISA method

An ELISA test was conducted on a polystyrene microtiter plate (Falcon 3915, produced by Becton Dickson Co.). The purified cord factor (TDM) antigen was dissolved in n-hexane to reach a concentration of 0.1 mg/ml. A 50 μl portion of this sample was added to each well (TDM 5 μg/well).

After plate drying at room temperature, 150 μl of an immunization blocking solution containing PBS-T was added to each well, and the plate was kept standing at room temperature for 1 hour in an incubator, followed by removal by suction. Then, 50 μg/well of a 160-fold serum dilution was added, and the plate was kept standing for 1 hour. Peroxidase-labeled goat antihuman IgG (500-fold dilution with PBS-T) was used as a secondary antibody (antiantibody). After the plate was kept standing for 1 more hour in an incubator, a substrate solution diluted so that 1 mg/ml of o-phenylenediamine was contained in a solution containing 0.1M citric acid, 0.2M $Na_2HPO_4$:$12H_2O$ and 0.04% aqueous hydrogen peroxide was added.

The reaction was terminated by the addition of 6N HCl, and absorbances at 492–630 nm were determined using a microplate reader. Each incubator was maintained at room temperature, and the plate was washed thrice with PBS-T during each reaction.

The experimental results were evaluated by ODD.

Results

Healthy humans: The average OD was 0.099, based on which ODD was calculated. The OD in the healthy humans ranged from 0.096 to 0.102, and none of them were judged to be positive.

Patients: Of the 50 acid-fast bacterial infection patients, 48 (43 of the 45 tubercule bacillus infection patients and all of the 5 atypical mycobacterial infection patients) were judged to be positive (ODD exceeding 0.100) (96% sensitivity).

Note that the average ODD in the tuberculosis patients was 1.273, and the average ODD in the atypical mycobacterial infection patients who were negative in the niacin test was 1.356. The ODD of the patients not infected with acid-fast bacteria having a cancer in one lung was 0.009, and they were judged to be negative.

None of the 55 healthy humans were judged to be positive (ODD exceeding 0.100).

These findings show that the antibody which reacts with the *M. tuberculosis*-derived cord factor (TDM) occurred in sera of patients positive in the acid-fast bacterial detection test, and was not detected in healthy humans (specificity 100%).

EXAMPLE 12

Using sera of 29 tuberculosis patients judged to be positive in Example 11, the procedure of Example 11 was followed except that the cord factor (TDM) used in Example 11 was replaced by the M. kan., M. int. or Nr-derived cord factor or trehalose-6,6'-dicorynomycolate (synthesized product). All these patients were judged to be positive to all the 4 antigens.

EXAMPLE 13

The procedure of Example 12 was followed using trehalose-6-monomycolates obtained from the bacterial cells described in Example 12. All samples were judged to be positive.

EXAMPLE 14

The procedure of Example 12 was followed except that the dilution rate of the sera of 29 tuberculosis patients judged to be positive in Example 11 was changed to 1280 folds. All samples were judged to be positive.

The present invention has been appropriately and thoroughly described in the above specification by means of Examples contained therein. It should be noted, however, that these may be altered or modified as long as the spirit or scope of the present invention is not hampered.

What is claimed is:

1. A method of diagnosing an infection caused by an acid-fast bacterium, which comprises conducting an immunoassay on a sample of body fluid of a target human with a reagent which consists essentially of at least one compound in the form of an immobilized solid phase and selected from the group consisting of:
    a) a mycolic acid obtained either by synthesis or by hydrolyzing acid-fast bacterial cells or a glycolipid extracted from acid-fast bacterial cells, followed by extraction and separation,
    b) a mycolic acid salt obtained by converting the mycolic acid of (a),
    c) a mycolic acid ester obtained by esterifying the mycolic acid of (a), the ester being a lower alkyl ester, a vinyl ester or a phenyl ester,
    d) a trehalose mycolic acid ester obtained either by synthesis or by extraction and separation from acid-fast bacterial cells, the ester being a trehalose dimycolate, a trehalose trimycolate or a trehalose tetramycolate, and
    e) a mycolic acid ester obtained either by synthesis or by extraction and separation from acid-fast bacterial cells, the ester being a glucose ester, a mannose ester or an arabinose ester, the reagent being one which specifically detects an antibody in the sample, which specifically binds to said compound, and the immunoassay comprises the steps of:
    (A) reacting (i) the reagent and (ii) the sample to form a complex wherein the antibody in the sample is bound to the compound immobilized on the solid phase, and then
    (B) detecting the presence of said complex with an enzyme-labeled antiantibody.

2. A method of claim 1 wherein the mycolic acid ester is a lower-alkyl ester.

3. A method of claim 1 wherein the mycolic acid ester is a glucose ester.

4. A method of claim 1 wherein the trehalose mycolic acid ester is a di- to tetra-substitution product of trehalose at a position or positions selected from the group consisting of the 2-, 2'-, 3-, 3'-, 6- and 6'-positions.

5. A method of claim 1 wherein the compound is derived from *tubercle bacillus*.

6. A method of claim 1 wherein the compound is derived from *Mycobacterium intracellulare*.

7. A method of claim 1 wherein the compound is derived from *Mycobacterium kansasii*.

8. A method of claim 1 wherein the compound is derived from *Nocardia rubra*.

9. A method of claim 1 wherein the compound is a mycolic acid.

10. A method of claim 1 wherein the compound is a mycolic acid salt.

11. A method of claim 1, wherein the immunoassay comprises the steps of:
    (A) reacting (i) the reagent and (ii) the sample to form a complex wherein the antibody in the sample is bound to the compound immobilized on the solid phase,
    (B) adding, after washing the complex formed in step (A), an enzyme-labeled antiantibody to bind the antiantibody to said complex,
    (C) removing unreacted enzyme-labeled antiantibody and assaying the enzyme activity on the solid phase; and then
    (D) comparing the assay value with the assay value obtained by the same steps on a body fluid of healthy human.

12. A method of claim 1 wherein step (B) comprises detecting the presence of said complex by reacting the complex with an enzyme-labeled antiantibody and determining the enzyme activity of the enzyme-labeled antiantibody which is bound to the complex.

13. A method of claim 12 wherein the enzyme activity is determined by subjecting the enzyme-labeled antiantibody, which is bound to the complex, to a color development reaction and determining a difference in optical density between a sample of body fluid of a healthy human and the sample of the target human.

14. A method of claim 1 wherein the compound is a separated trehalose tetramycolate.

15. A method of claim 1 wherein the compound is a synthetic compound.

16. A method of claim 1 wherein the compound is a separated trehalose dimycolate.

17. A method of claim 1 wherein the compound is a separated trehalose trimycolate.

18. A method of claim 1 wherein the compound is 6,6'-di-O-mycoloyl-α,α-trehalose.

* * * * *